(12) United States Patent
Hasken et al.

(10) Patent No.: US 7,380,464 B2
(45) Date of Patent: Jun. 3, 2008

(54) OUT-OF-PLAIN STRAIN ELIMINATION ACOUSTIC WAVE TORQUE SENSOR

(75) Inventors: Randall J. Hasken, Lanark, IL (US); Larry J. Bohnert, Monroe, WI (US); Steven J. Magee, Lena, IL (US)

(73) Assignee: Honeywell International Inc., Morristown, NJ (US)

( * ) Notice: Subject to any disclaimer, the term of this patent is extended or adjusted under 35 U.S.C. 154(b) by 77 days.

(21) Appl. No.: 11/299,023

(22) Filed: Dec. 8, 2005

(65) Prior Publication Data

US 2007/0137309 A1 Jun. 21, 2007

(51) Int. Cl.
*G01N 29/04* (2006.01)
*G01L 3/02* (2006.01)

(52) U.S. Cl. .................... 73/801; 73/862.191

(58) Field of Classification Search ............. 73/649, 73/650, 801, 862.191; 340/446
See application file for complete search history.

(56) References Cited

U.S. PATENT DOCUMENTS

| | | | | |
|---|---|---|---|---|
| 4,398,117 | A * | 8/1983 | St. Cyr ................. 310/348 |
| 4,785,674 | A | 11/1988 | Orman et al. ........... 73/862.17 |
| 4,823,617 | A | 4/1989 | Hase et al. ............. 73/862.36 |
| 4,852,411 | A | 8/1989 | Beihoff ................. 73/862.36 |
| 4,911,023 | A | 3/1990 | Izumi et al. |
| 5,146,790 | A | 9/1992 | Fish ..................... 73/862.336 |
| 5,303,593 | A | 4/1994 | Kremidas ............... 73/708 |
| 5,821,425 | A * | 10/1998 | Mariani et al. .......... 73/703 |
| 5,861,558 | A | 1/1999 | Buhl et al. ............. 73/777 |
| 6,269,702 | B1 * | 8/2001 | Lambson ............... 73/862.045 |
| 6,412,356 | B1 | 7/2002 | Kouketsu et al. ....... 73/862.333 |
| 6,439,066 | B1 | 8/2002 | Norton ................. 73/862.333 |
| 6,601,462 | B1 | 8/2003 | Ueno et al. ............ 73/862.337 |
| 6,675,663 | B1 | 1/2004 | Irion et al. ............ 73/862.627 |
| 6,817,253 | B2 * | 11/2004 | Gandrud ............... 73/862.23 |
| 6,991,584 | B2 * | 1/2006 | Cowan ................. 477/110 |
| 7,095,198 | B1 * | 8/2006 | O'Brien ............... 318/432 |
| 2002/0002875 | A1 * | 1/2002 | Kochanowski et al. ... 74/572 |
| 2003/0231107 | A1 * | 12/2003 | Edmonson et al. ..... 340/10.42 |

(Continued)

FOREIGN PATENT DOCUMENTS

DE 4208522 A1 9/1993

(Continued)

OTHER PUBLICATIONS

"Flywheel." Webster's Third New International®, Unabridged. Merriam-Webster, Inc. Copyright 1993.*

*Primary Examiner*—Edward Lefkowitz
*Assistant Examiner*—Punam Patel
(74) *Attorney, Agent, or Firm*—Kermit D. Lopez; Luis M. Ortiz

(57) ABSTRACT

A torque sensor is disclosed based on a SAW die configured on a surface of a plate, and an isolator formed from a flexible material. The isolator is rigidly mounted to the plate, such that the isolator flexes when a force perpendicular to the surface of the plate are applied while transferring a torque that is applied within a plane of the plate to the SAW die, thereby eliminating or minimizing the effect on the SAW die of out-of-plane forces on the plate so as to isolate the torque transferred to the plate.

13 Claims, 7 Drawing Sheets

U.S. PATENT DOCUMENTS

| | | | |
|---|---|---|---|
| 2004/0027228 A1 | 2/2004 | Stevens ........................ 338/2 |
| 2004/0239475 A1 | 12/2004 | Hermann et al. ............. 338/25 |
| 2005/0068989 A1 | 3/2005 | Herbert et al. ............. 370/506 |
| 2007/0039396 A1* | 2/2007 | Bunyer et al. ................ 73/819 |
| 2007/0125184 A1* | 6/2007 | Maguire et al. ......... 73/862.37 |

FOREIGN PATENT DOCUMENTS

| | | | |
|---|---|---|---|
| EP | 0518900 B1 | | 12/1992 |
| GB | 2096777 A | | 10/1982 |
| GB | 2393521 | * | 3/2004 |
| JP | 59060332 A | | 4/1984 |
| WO | WO 91/13832 | | 9/1991 |
| WO | WO 91/13832 A | | 9/1991 |
| WO | WO 00/26625 A1 | | 5/2000 |
| WO | WO 03/082527 | * | 10/2003 |
| WO | WO 2006/018607 A1 | | 2/2006 |

* cited by examiner

OUT-OF-PLAIN STRAIN ELIMINATION ACOUSTIC WAVE TORQUE SENSOR

TECHNICAL FIELD

Embodiments are generally related to sensing devices and in particular, to surface acoustic wave (SAW) sensors that measure the mechanical qualities of various structures. Embodiments are additionally related to sensing devices utilized in torque detection.

BACKGROUND

Passive sensors employing acoustic wave components for measuring torque are well known in the art. Torque measurement devices are an emerging technology with varied applications in automotive, transportation, rail and other similar segments for use in transmission and chassis applications, to name a few. Acoustic wave sensors are so named because they use a mechanical or acoustic wave as the sensing mechanism. As the acoustic wave propagates through or on the surface of the material, any changes to the characteristics of the propagation path affect the velocity, phase, and/or amplitude of the wave.

Working at very high frequencies, these extremely high-quality value (high Q value) sensing devices can be wirelessly excited with an interrogation pulse and a resonant frequency response measured allowing strain to be calculated. Torque can be sensed by using appropriate packaging and algorithms to deduce the value of the sensed property from the returned signal. These devices are cost-effective to manufacture, remarkably stable, and offer significantly higher performance than their 20$^{th}$ century, resistance gauge counterparts.

Unlike a conventional wire strain gauge, an acoustic wave torque sensor can store energy mechanically. Once supplied with a specified amount of energy (e.g., via radio frequency), these devices can function without cumbersome oscillators or auxiliary power sources. This capability has been exploited in many wireless/passive sensing operations, such as tire pressure sensors, and optimization of power-train efficiency.

When an acoustic wave device is used in sensor applications, the effect of an electric pulse applied to the interdigital transducers (IDTs) is to cause the device to act as a transducer. The electric signal is converted to an acoustic wave which is transmitted via the piezoelectric substrate to the other IDTs. Upon arrival of the acoustic wave at the IDTs, the transducing process is reversed and an electric signal is generated. This output signal has a characteristic resonant frequency, or delay time which is dependent upon a number of factors including the geometry of the IDT spacing. Since the IDT spacing varies with strain/stress when the substrate is deformed, any change in this condition can be monitored by measuring the acoustic wave device frequency or delay time.

One of the problems with currently implemented torque sensors is the effect on the utilized SAW die of out-of-plane forces during torque sensing operations. Such out-of-plane forces tend to damage the resulting torque sensor, or at the very least, result in numerous torque sensor error readings. A need therefore exists for an improved apparatus or method for eliminating or minimizing such an effect on a SAW die utilized in torque sensor devices.

BRIEF SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention is to provide for an improved sensing device and method.

It is another aspect of the present invention to provide for an improved torque sensor apparatus.

The aforementioned aspects of the invention and other objectives and advantages can now be achieved as described herein. A torque sensor is disclosed based on a SAW die configured on a surface of a plate, and an isolator formed from a flexible material. The isolator is rigidly mounted to the plate, such that the isolator flexes when a force perpendicular to the surface of the plate are applied while transferring a torque that is applied within a plane of the plate to the SAW die, thereby eliminating or minimizing the effect on the SAW die of out-of-plane forces on the plate so as to isolate the torque transferred to the plate.

The torque sensor described herein eliminates or minimizes the effect of a SAW die of out-of-plane forces on a plate or disk so as to isolate the true torque transferred through the plate. The SAW die can then be mounted in the path of the isolated torque. Such a torque sensor solves the problem the aforementioned problem by placing the SAW die on an isolator device that is rigidly mounted to the plate by welding, bolding, pinning, etc., with attachment end points located along the radius of the plate and in the torque path. The isolator can be configured, such that it can flex freely in the direction of the out-of-plane forces, while remaining rigid in the path of the torque.

The isolator can be configured from a thin or necked down material that flexes, and therefore isolates, when forces perpendicular to the surface of the plate are applied while transferring force (e.g., torque) that is applied within the plane of the plate or disk to the SAW die. The isolator can be constructed either integral to the RF coupler or separate from it.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
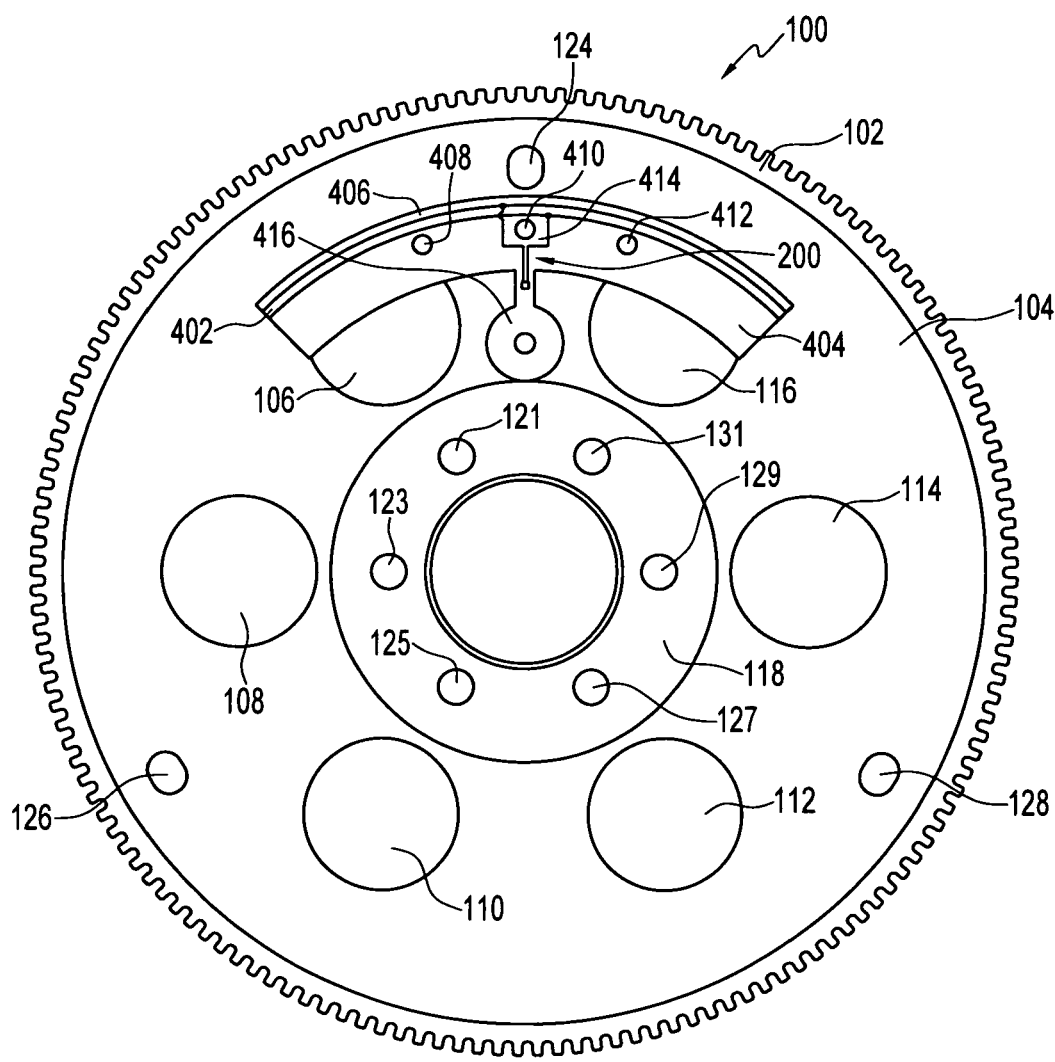
FIG. 1 illustrates a view of a flex plate than can be adapted for use with a torque sensor apparatus in accordance with a preferred embodiment.

FIG. 1 illustrates a view of a flex plate 100 than can be adapted for use with a torque sensor apparatus in accordance with a preferred embodiment. Note that in FIGS. 1-5, identical or similar parts or elements are generally indicated by identical reference numerals. Although flex plate 100 is illustrated in FIG. 1 in accordance with an example embodiment, it can be appreciated that any radial disk could be used to transmit torque as provided by the depicted embodiments. Flex plate 100 generally includes a ridged portion 102 that surrounds a circular section 104 that in turn includes a plurality of holes 106, 108, 110, 112, 114, 116 and 124, 126, 128 formed therein. The ridged portion 102 and the circular section 104 can function as, for example, a ring gear, depending upon design considerations.

Holes 106, 108, 110, 112, 114 and 116 can function as through holes and can be optionally utilized, depending on design goals. Holes 124, 126, and 128, on the other hand, can constitute flex plate to torque converter mounting holes. A group of flex plate to crank mounting holes 121, 123, 135, 127, 129, and 123 can also be provided at a central portion 118 that is located centrally within circular portion 104. Flex plate 100 is thus illustrated as an example of a flexible component that can be utilized to transmit torque, depending on design considerations.

Figure 3:
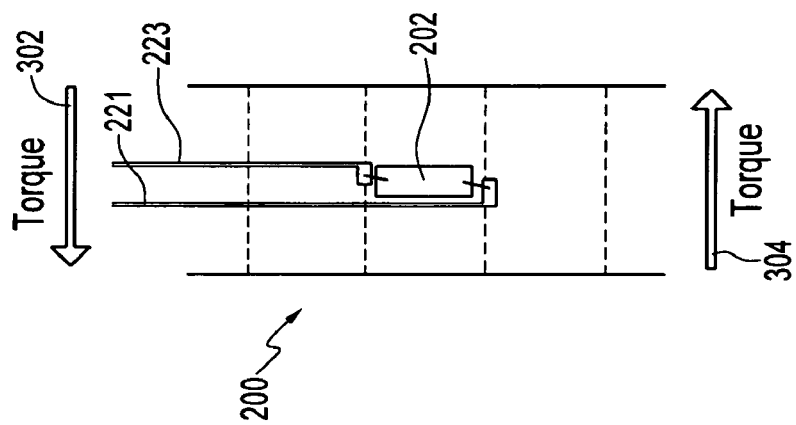
FIG. 3 illustrates a radial view of the torque sensor apparatus depicted in FIG. 1 in accordance with a preferred embodiment.
Figure 2:
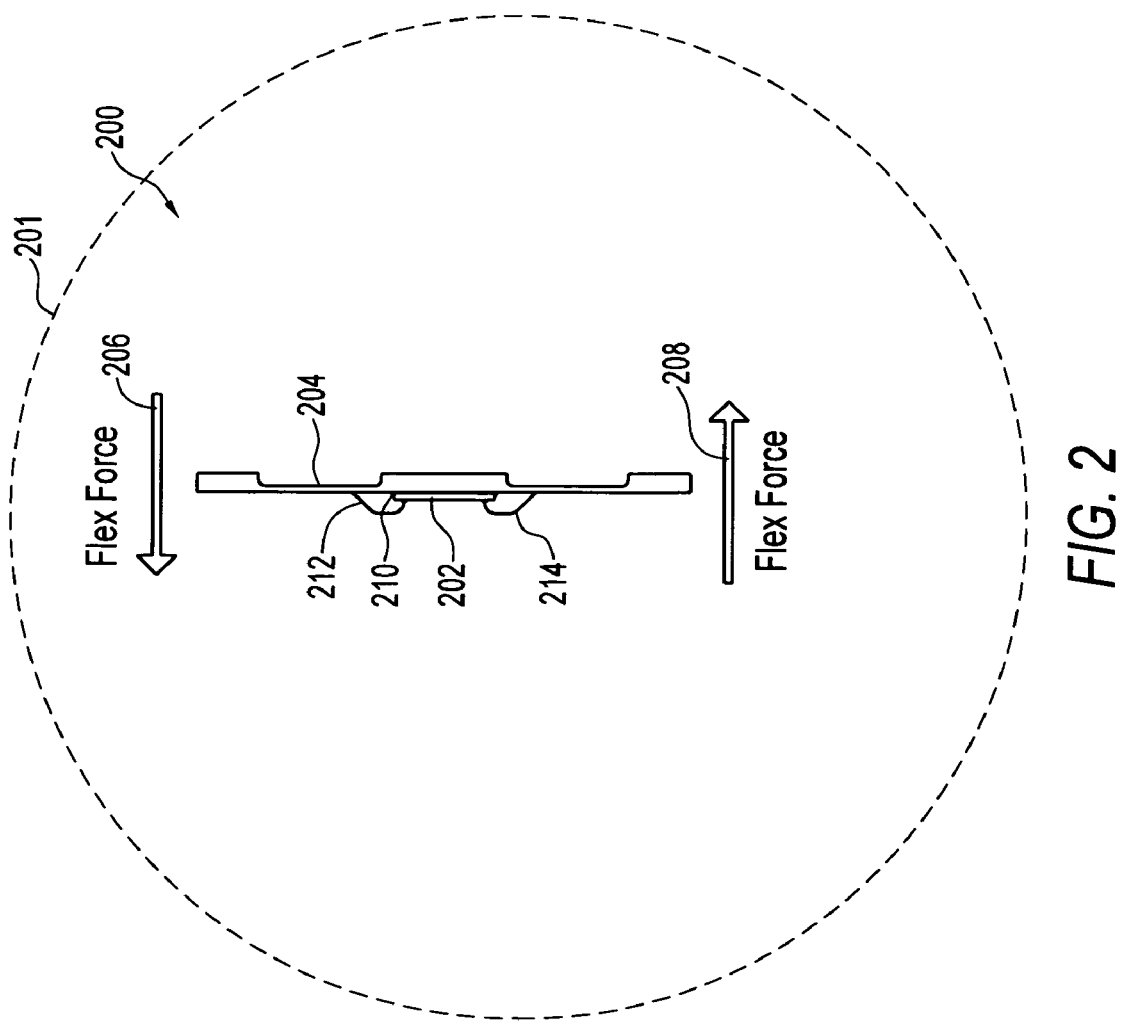
FIG. 2 illustrates a side view of a torque sensor apparatus that can be implemented in accordance with a preferred embodiment.

FIG. 2 illustrates a side view of a torque sensor apparatus 200 that can be implemented in accordance with a preferred embodiment. FIG. 3 illustrates a radial view of the torque sensor apparatus 200 depicted in FIG. 1 in accordance with a preferred embodiment, As indicated in FIG. 2, the torque sensor apparatus 200 is disposed within the outlines of a generally circular area as indicated by the dashed circular line 201. A SAW die 202 can be configured on the surface of, for example, the plate 100 depicted in FIG. 1.

An isolator 204 can be provided, which is formed from a flexible material. The isolator 204 is rigidly mounted to the plate 100 depicted in FIG. 1 and FIG. 8. The isolator 204 flexes when a force is applied perpendicular to the surface of the plate 100, resulting in a transfer of torque applied within the plane of the plate 100 to the SAW die 202, thereby eliminating or minimizing the effect on the SAW die 202 of out-of-plane forces on the plate 100 so as to isolate the torque transferred to the plate.

Figure 4:
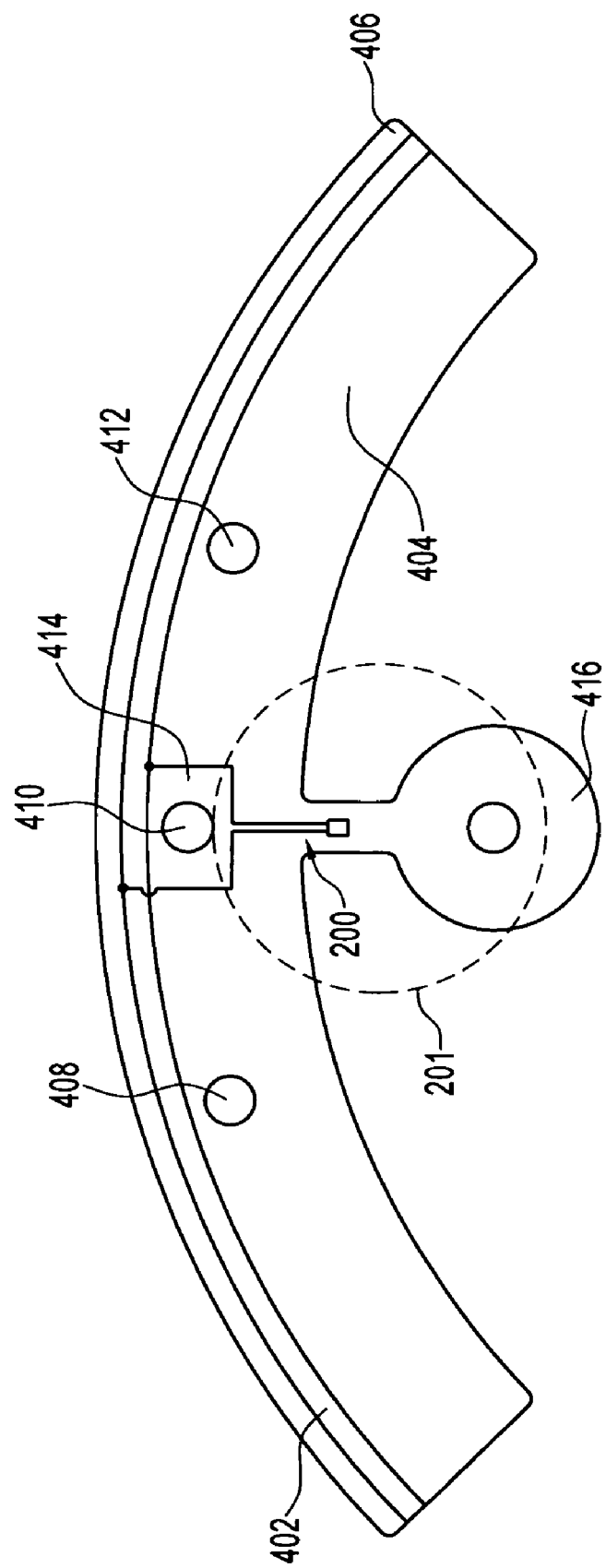
FIG. 4 illustrates a sectional view of the torque sensor apparatus depicted in FIGS. 1-3, in accordance with a preferred embodiment.
Figure 7:
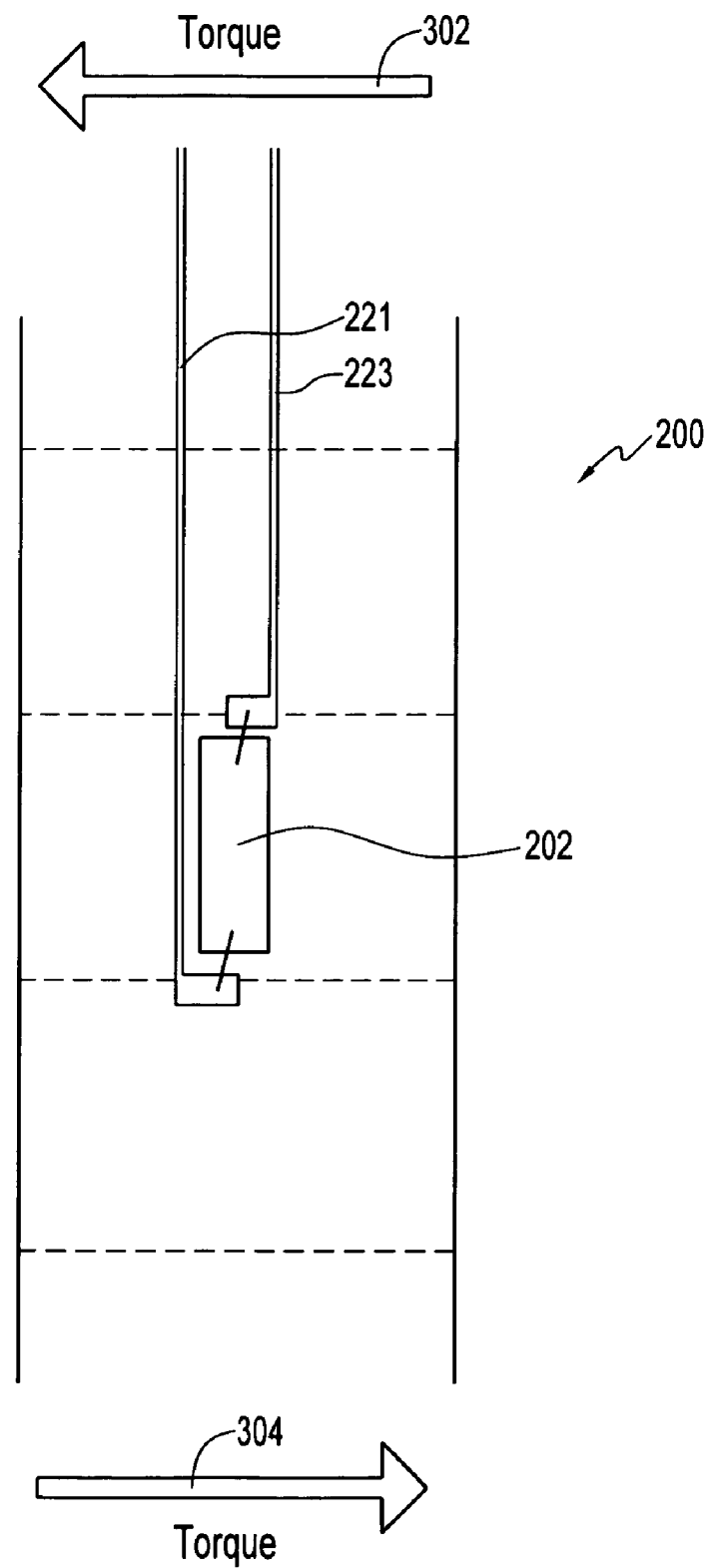
FIG. 7 illustrates a detailed view of the configuration depicted in FIG. 3, in accordance with a preferred embodiment.
Figure 8:
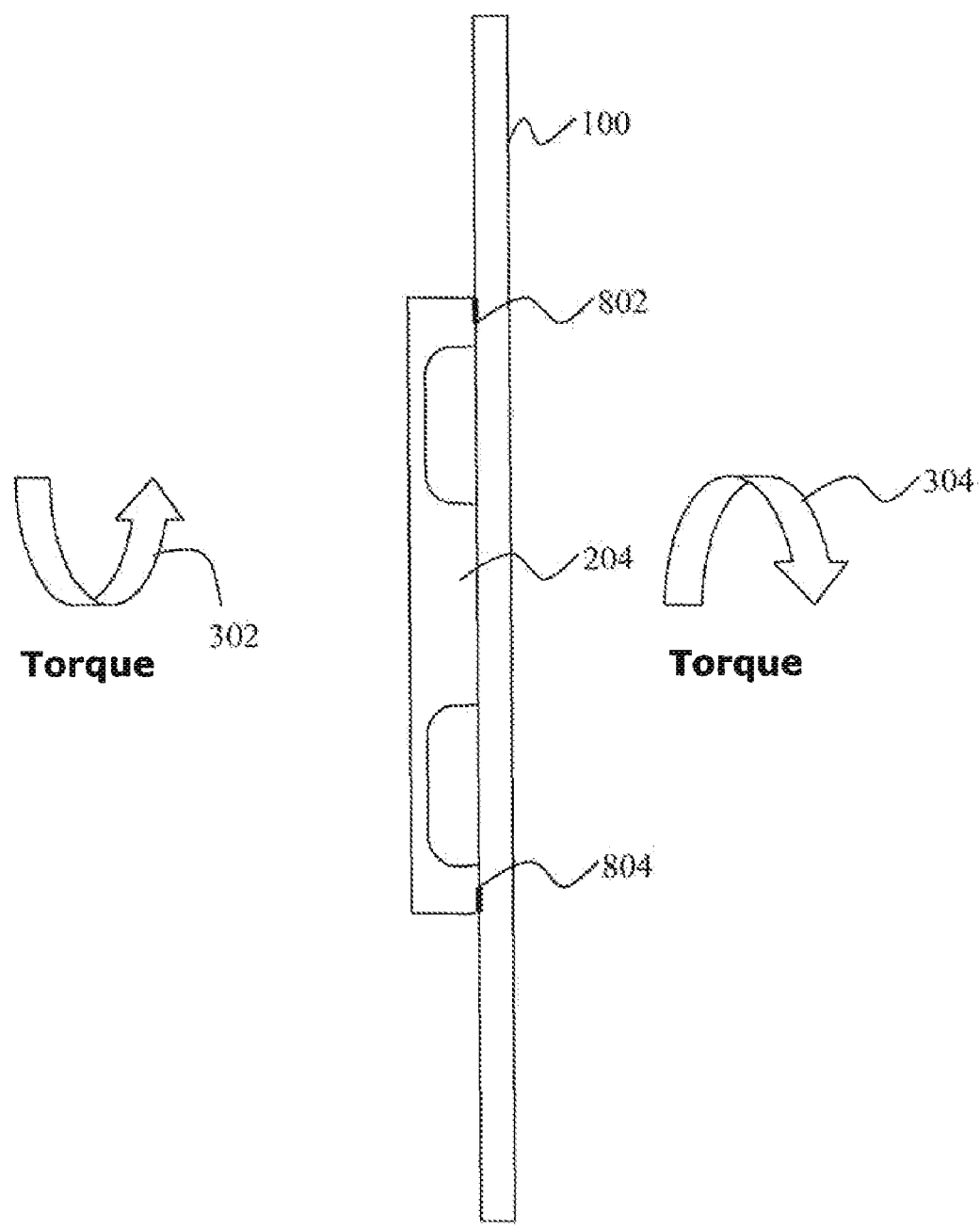
FIG. 8 illustrates a side view of the isolator rigidly mounted in the path of the torque to the flex plate by a plurality of attachment endpoints, in accordance with the disclosed embodiments.

Torque is depicted by arrows 302, 304 illustrated in FIG. 3 and FIG. 8, while arrows 206 and 208 depicted in FIG. 4 represent a flex force. In general, the cross sectional configuration of isolator 204 tends to minimize strain transfer due to flexing of the flex plate 100 depicted in FIG. 1. This flexing is indicated by arrows 206, 208 in FIG. 2. The SAW die 202 is generally connected to wire bonds 212, 214. An adhesive 210 can be utilized to connect the SAW die 202 to the isolator 204. Note that in FIG. 3, conductors 221, 223 are additionally illustrated, which can communicate with antenna elements. A detailed view of the configuration depicted in FIG. 3 is also illustrated in FIG. 7.

FIG. 4 illustrates a sectional view of the torque sensor 200 apparatus depicted in FIGS. 1-3, in accordance with a preferred embodiment. The flexible isolator 204 of the torque sensor apparatus 200 is generally located within the bounds of the dashed circular line 201 illustrated in FIG. 4. One end 416 of the isolator portion 200 is connected to an antenna portion 404, which in turn is connected to a Printed Circuit Board (PCB) or substrate 402 upon which an antenna element 406 can be located. Mounting holes 408, 410, 412 can be formed within the antenna portion 404.

Figure 5:
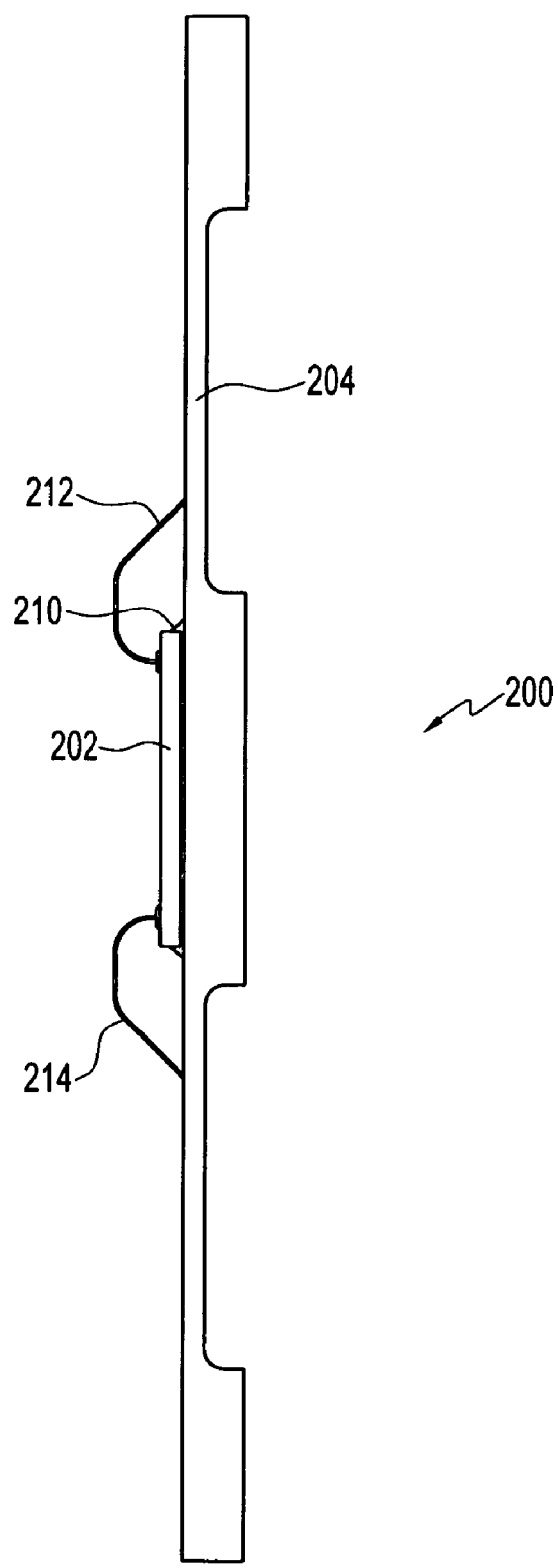
FIG. 5 illustrates a side cross-sectional view of the torque sensor apparatus depicted in FIGS. 1-4, in accordance with a preferred embodiment.

FIG. 5 illustrates a side cross-sectional view of the torque sensor apparatus 200 depicted in FIGS. 1-4, in accordance with a preferred embodiment. In general, the SAW die 202 is placed on the isolator 204. The SAW die 202 is rigidly mounted to isolator 204 by adhesive with attachment end points 802, 804 located along the radius of plate 100 depicted in FIG. 1 and FIG. 8 and in the path of the torque indicated by arrows 302, 304 in FIG 8. The isolator 204 can be constructed that it flexes freely in the direction of the out-of-plane forces while remaining rigid in the path of the torque. The torque sensor apparatus 200 can be constructed from a thin or necked down material that will flex, and therefore isolate, when forces perpendicular to the surface of the plate 100 are applied while transferring force (i.e., torque) that is applied within the plane of the disk or plate 100 to the SAW die 202. The isolator 204 can be formed to operate with an RF coupler, such as the antenna elements or antenna portions 404 and/or 406 and the transceiver portion 414 depicted in FIG. 4.

Figure 6:
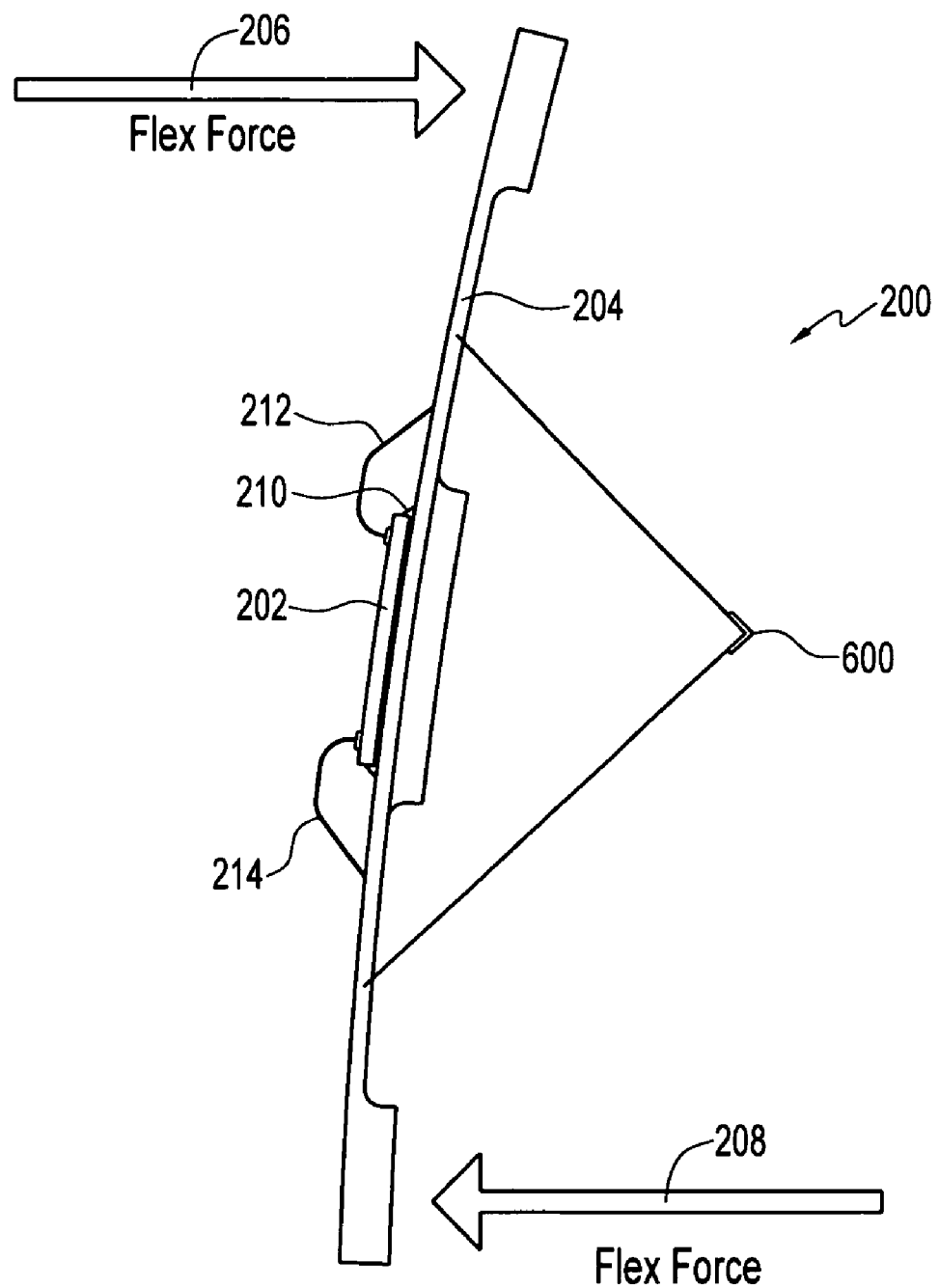
FIG. 6 illustrates an exploded view of the torque sensor apparatus in a flexible position, in accordance with a preferred embodiment.

FIG. 6 illustrates an exploded view of the torque sensor apparatus 200 in a flexible position, in accordance with a preferred embodiment. Note that in FIGS. 1-7, identical or similar parts or elements are generally indicated by identical reference numerals. The configuration depicted in FIG. 6 demonstrates that a reduced cross section 600 can minimize out-of-plane forces due to flexing of the flex plate 100 described earlier, as indicated by the flex force indicated by arrows 206 and 214. FIG. 7 illustrates a detailed view of the configuration depicted in FIG. 3, in accordance with a preferred embodiment. FIG. 7 illustrates how torque (i.e., see arrows 302 and 304) acts lateral to the conductors 221, 223 and the SAW die 202 and the resulting sensor. FIG. 8 illustrates a side view of the isolator 204 rigidly mounted in the path of the torque 302, 304, to the flex plate 100 by a plurality of attachment endpoints 802, 804.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A torque sensor apparatus, comprising:
    a SAW die configured on a surface of a plate; and
    a flexible isolator formed from a flexible material, wherein said flexible isolator is rigidly mounted to said plate, such that said flexible isolator flexes when a force perpendicular to said surface of said plate is applied while transferring a torque that is applied within a plane of said plate to said SAW die, wherein said flexible isolator is configured to remain rigid in a path of said torque, thereby eliminating or minimizing an effect on said SAW die of out-of-plane forces on said plate so as to isolate said torque transferred to said plate.

2. The apparatus of claim 1 wherein said flexible isolator is rigidly mounted to said plate by welding said flexible isolator to said plate.

3. The apparatus of claim 1 wherein said flexible isolator is rigidly mounted to said plate by bolting said flexible isolator to said plate.

4. The apparatus of claim 1 wherein said flexible isolator is rigidly mounted to said plate by pinning said flexible isolator to said plate.

5. The apparatus of claim 1 wherein said flexible isolator is rigidly mounted to said plate with a plurality of attachment end points located along a radius of said plate and in a path of said torque.

6. The apparatus of claim 1 further comprising an RF coupler associated with said isolator.

7. The apparatus of claim 1 wherein said flexible material comprises a thin material that flexes to isolate said torque.

8. A torque sensor apparatus, comprising:
   a SAW die configured on a surface of a plate;
   an isolator formed from a flexible material, wherein said isolator is rigidly mounted to said plate with a plurality of attachment end points located along a radius of said plate and in a path of said torque; and
   an RF coupler associated with said isolator, wherein said isolator flexes when a force perpendicular to said surface of said plate are applied while transferring a torque that is applied within a plane of said plate to said SAW die, thereby eliminating or minimizing an effect on said SAW die of out-of-plane forces on said plate so as to isolate said torque transferred to said plate.

9. The apparatus of claim 8 wherein said isolator is configured to remain rigid in a path of said torque.

10. The apparatus of claim 9 wherein said SAW die is mounted in a said path of said torque.

11. A torque sensor method, comprising:
    forming an isolator from a flexible material;
    configuring a SAW die on a surface of a plate;
    rigidly mounting said isolator to said plate;
    applying a force perpendicular to said surface of said plate, such that said isolator flexes while transferring a torque applied within a plane of said plate to said SAW die; and
    mounting said SAW die in a path of said torque, thereby eliminating or minimizing an effect on said SAW die of out-of-plane forces on said plate so as to isolate said torque transferred to said plate.

12. The method of claim 11 wherein said isolator is rigidly mounted to said plate with a plurality of attachment end points located along a radius of said plate and in a path of said torque.

13. The method of claim 11 further comprising configuring said isolator to flex freely in a direction of said out-of-plane forces while remaining rigid in a path of said torque.

\* \* \* \* \*